United States Patent [19]

Harris

[11] Patent Number: 4,525,474

[45] Date of Patent: Jun. 25, 1985

[54] INSECTICIDAL N-SUBSTITUTED-2-(NITROMETHYLENE)-TETRAHYDRO-2H-1,3-THIAZINES

[75] Inventor: Martin Harris, Sittingbourne, England

[73] Assignee: Shell Oil Company, Houston, Tex.

[21] Appl. No.: 650,610

[22] Filed: Sep. 14, 1984

[30] Foreign Application Priority Data

Sep. 14, 1983 [GB] United Kingdom ................. 8324664

[51] Int. Cl.$^3$ ..................... C07D 279/06; A01N 43/86
[52] U.S. Cl. ....................................... 514/226; 544/54

[58] Field of Search ........................... 544/54; 424/246

[56] References Cited

U.S. PATENT DOCUMENTS 4,483,856  11/1984  Harris et al. ......................... 544/54
4,486,427  12/1984  Estreicher et al. ................... 544/54

Primary Examiner—John M. Ford

[57] ABSTRACT

Insecticidal 2-(nitromethylene)-tetrahydro-2H-1,3-thiazines substituted on the nitrogen atom of the ring by a hydroxy- or formyloxy-substituted alkylsulfonyl moiety.

6 Claims, No Drawings

INSECTICIDAL N-SUBSTITUTED-2-(NITROMETHYLENE)-TETRAHYDRO-2H-1,3-THIAZINES

DESCRIPTION OF THE INVENTION

It has been found that useful insecticidal activity is possessed by compounds of the formula:

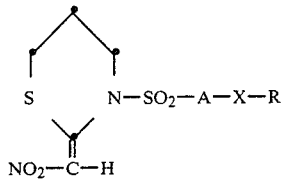

(I)

wherein A is an alkylene moiety of from one to ten carbon atoms, X is oxy (—O—) or thio (—S—) and R is hydrogen or formyl (—C(O)H).

The alkylene moiety, A, may be either straight-chain or branched-chain in formation, and preferably contains from two to six carbon atoms.

Preferably, X represents oxy (—O—).

The compounds of Formula I may exist as either of two geometric (cis-trans), isomers, depending upon the spatial configuration about the double bond between the carbon atom of the nitromethylene moiety and the ring carbon to which it is bonded. The insecticidal activities of the individual isomers may differ. In the cases of the individual species whose preparation is described in the examples, hereinafter, the isomeric content and configuration of the products have not been ascertained. The invention contemplates all of the insecticidally active isomers, and mixtures thereof, both those which result from the method of synthesis, and those which have been deliberately created.

Compounds of Formula I can be prepared by treating 2-(nitromethylene)-tetrahydro-2H-1,3-thiazine of the formula

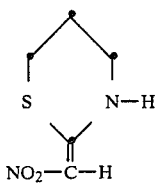

(II)

with the appropriate sulfonyl halide, R—Y—A—SO$_2$—Hal wherein Hal is bromine or chlorine, in an inert solvent, in an inert atmosphere, and in the presence of a tertiary amine base as hydrogen halide acceptor. Suitable solvents are haloalkanes, such as methylene chloride, and ethers, such as tetrahydrofuran, or dimethylformamide. The reaction proceeds at satisfactory rates at low temperatures, for example, below 0° C., with temperatures of from about −10° C. to about −75° C. being particularly suitable. Suitable amine bases include trimethylamine, triethylamine and N-ethyl-N,N-diisopropylamine. Preferably, the reaction is moderated by employing a solution of the sulfonyl halide in the solvent and adding the solution slowly to the stirred solution of the compound of Formula III and the amine. The products are isolated and purified by conventional procedures and techniques.

Compounds of Formula I in which R represents formyl, may be prepared by an alternative procedure which comprises treating a compound of the formula

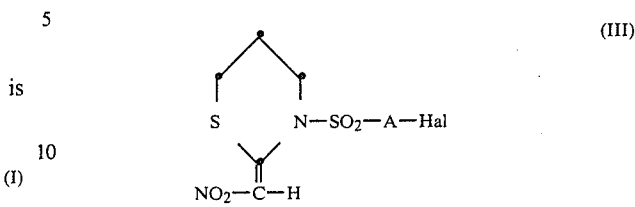

(III)

with a salt, especially an alkali metal salt, of formic acid. Compounds of Formula III and their preparation are described and claimed in U.S. patent application Ser. No. 478,600, which has been allowed, now U.S. Pat. No. 4,483,856.

It may be convenient to prepare compounds of Formula I in which R represents hydrogen by hydrolysis of a compound in which R represents formyl.

Compound II and its preparation are described in U.S. Pat. No. 3,993,648. The sulfonyl halides, R—X—A—SO$_2$—Hal, are known compounds.

The preparation, isolation and physical properties of typical individual species of the compounds of Formula I, in particular instances, are described in the following examples. In each case, the identity of the product, and each of any intermediate involved, was confirmed by appropriate chemical and spectral analyses.

EXAMPLE 1

N-(3-formyloxypropylsulfonyl)-2-(nitromethylene)-tetrahydro-2H-1,3-thiazine (1)

5 ml of triethylamine was added to a solution of 4.8 g of 2-(nitromethylene)-tetrahydro-2H-1,3-thiazine in 100 ml of dichloromethane at −15° C. under nitrogen. Then a solution of 5.9 g of 3-chloropropylsulfonyl chloride in 50 ml of dichloromethane was added drop-by-drop over 25 minutes. The resulting mixture was allowed to warm to room temperature, stirred for one hour and washed with 2% hydrochloric acid solution. The organic phase was separated, dried (MgSO$_4$) and the solvent was evaporated under reduced pressure. The residue was triturated with methanol to give N-(3-chloropropylsulfonyl)-2-(nitromethylene)-tetrahydro-2H-1,3-thiazine (1A), as a solid, m.p.: 99°–99° C.

A mixture of 10 g of 1A, 700 ml of acetone and 17.6 g of sodium iodide was refluxed for 16 hours. Then the solvent was evaporated under reduced pressure and the residue was partitioned between water and dichloromethane. The dichloromethane phase was separated, dried (MgSO$_4$) and the solvent was evaporated under reduced pressure. The residue was recrystallized from dichloromethane to give N-(3-iodosulfonyl)-2-(nitromethylene)-tetrahydro-2H-1,3-thiazine (1B), as a yellow crystalline solid, m.p.: 106°–109° C.

4 g of 1B was added to a mixture of 4 g of sodium formate and 20 ml of hexamethylphosphoramide at 0° C. under nitrogen. The resulting mixture was allowed to warm to room temperature and stirred for 18 hours. Then it was poured into 610 ml of ether, the resulting solution was washed with brine, dried (MgSO$_4$) and the solvent was evaporated under reduced pressure, to give 1, as a solid, m.p.: 89° C.

EXAMPLE 2

N-(3-hydroxypropylsulfonyl)-2-(nitromethylene)-tetrahydro-2H-1,3-thiazine (2)

2 g of 1 was elected through a column of 200 g of neutral alumina, using a 19:1 v:v mixture of dichloromethane and methanol as eluent. The fractions containing 2 were stripped of solvent under reduced pressure and the combined residue was triturated with ether, to give 2, as a solid, m.p.: 80°–83° C.

EXAMPLES 3–6

By the procedures described in Examples 1 and 2, the following further individual species of the compounds of Formula I were prepared from the appropriate precursors. These species are identified in terms of their constituent moieties, A, X and R, and their melting points, given in Table 1.

TABLE 1

| Example No. | Compound No. | A | X | R | Melting Point (C.°) |
|---|---|---|---|---|---|
| 3 | 3 | $-(CH_2)_4-$ | $-O-$ | $-C(O)H$ | 76 |
| 4 | 4 | $-(CH_2)_4-$ | $-O-$ | H | 76 |
| 5 | 5 | $-(CH_2)_5-$ | $-O-$ | $-C(O)H$ | 90 |
| 6 | 6 | $-(CH_2)_5-$ | $-O-$ | H | 114–115 |

Compounds of Formula I have been found to possess useful insecticidal activity, and to be comparatively stable to light and oxidation. Compounds of Formula I are of particular interest for control of the larval (caterpillar or "worm") forms of insects of the genus Heliothis, such as *H. zea* (corn earworm, cotton bollworm, tomato fruitworm), the genus Spodoptera, such as *S. littoralis* (Egyptian cotton leafworm).

Accordingly, this invention includes a method for controlling insect pests at a locus which comprises applying to the locus an effective amount of at least one compound of Formula I. For such use, the active compound is ordinarily most effectively applied when formulated with a carrier, or surface-active agent, or both. Therefore, this invention also includes pesticidal compositions which comprise a carrier, or a surfactant or both, together with a pesticidally effective amount of at least one compound of Formula I.

The term "carrier" as used herein means an inert, horticulturally acceptable material (i.e., non-phytotoxic when applied to plants), that may be inorganic or organic and of synthetic or natural origin with which the active compound is mixed of formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example superphosphates.

Suitable liquid carriers include solvents for the compound of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified, normally vaporous, gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols; encapsulated formulations and controlled release formulations are also contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10%w of toxicant. Granules may be manufactured by extrusion of plastics, agglomeration or impregnation techniques. Generally, granules will contain 0.5–25%w toxicant and 0–10%w of additives such as stabilizers, slow release modifiers and binding agents. Emulsifiable concentrates usually contain, in addition to the solvent, and when necessary, cosolvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

The thermal stability of the compounds and compositions of the invention may often be improved by the addition of stabilizing amounts, usually 10–100%w based on the active compound, of certain organo nitrogen compounds such as urea, dialkylureas, thiourea or guanidine salts or alkali metal salts of weak acids such as bicarbonates, acetates or benzoates.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of toxicants of this invention at the locus to be protected—i.e. the applied dosage—is of one order of 0.01% to 0.5% based on the total weight of the formulation, though under some circumstances the effective concentration will be as little as 0.001% or as much as 2%, on the same basis.

Activity of individual species of Formula I with respect to insect pests was determined by using standardized test methods to ascertain the toxicity of the compounds as follows:

The insecticidal activities of individual species of Formula I were assessed with respect to the Egyptian cotton leafworm (*Spodoptera littoralis*), as follows:

In each test a 0.2% solution or suspension of each test compound in 16.7% acetone in water containing 0.04% Triton X-100 (as surfactant) was used, as were control solutions of water, acetone and Triton S-100 in the same proportions. The tests were all conducted under normal insectary conditions 23° C.±2° C. (fluctuating light and humidity). Each test solution and the control solution was sprayed onto a separate petri dish containing a diet on which the *S. littoralis* larvae had been reared. When the spray deposit had dried each dish was infested with ten second instar larvae. Mortality assessments were made 1 and 7 days after spraying and the percentage mortality calculated.

In each instance, the toxicity of the compound of the invention was compared to that of a standard pesticide (Parathion), its relative toxicity then being expressed in terms of the relationship between the amount of compound of the invention and the amount of the standard pesticide required to produce the same percentage (50) of mortality in the test insect. By assigning the standard pesticide an arbitrary rating of 100, the toxicities of the compounds of the invention were expressed in terms of the toxicity indices, which compares the toxicity of the compounds of the invention with that of the standard pesticide. That is to say, a test compound having a Toxicity Index of 50 would be half as active, while one having a Toxicity Index of 200 would be twice as active as the standard pesticide. The Toxicity Indices are set forth in Table 2.

TABLE 2

| Compound No. | Toxicity Index |
|---|---|
| 1 | 109 |
| 2 | 110 |
| 3 | 70 |
| 4 | 65 |
| 5 | 46 |
| 6 | 83 |

The insecticidal activities of individual species of Formula I were assessed with respect to the corn earworm (*Heliothis zea* (Boddie)), as follows:

Corn earworm larvae were tested by spraying a broad bean plant with dilutions of acetone solution of test compound into water containing an emulsifier. Immediately after spraying, 5 larvae were transferred to the plant and held for 44–46 hours, at which time the dead and moribund larvae were counted. The tests were conducted employing several different dosage rates for each test compound. Two replicates were conducted. The results were expressed in terms of the Toxicity Index in each case. The results are presented in Table 3.

TABLE 3

| Compound No. | Toxicity Index |
|---|---|
| 1 | 2500 |
| 2 | 2500 |
| 3 | 3000 |
| 4 | 2770 |
| 5 | 4100 |
| 6 | 1560 |

I claim:
1. A compound of the formula

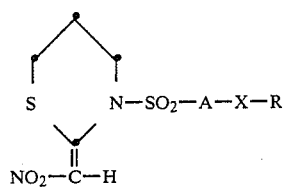

wherein A is an alkylene moiety of from one to ten carbon atoms, X is oxy (—O—) or thio (—S—) and R is hydrogen or formyl (—C(O)H).

2. A compound according to claim 1 wherein A contains from two to six carbon atoms and X is oxy.

3. A method for controlling insects at a locus which comprises applying to said locus an effective amount of a compound of claim 1.

4. A method for controlling insects at a locus which comprises applying to said locus an effective amount of a compound of claim 2.

5. An insecticidal composition comprising an effective amount of a compound of claim 1 together with a horticulturally accceptable carrier and optionally a surface-active agent.

6. An insecticidal composition comprising an effective amount of a compound of claim 2 together with a horticulturally acceptable carrier, and optionally a surface-active agent.

* * * * *